United States Patent
Basu

(10) Patent No.: US 9,810,672 B2
(45) Date of Patent: Nov. 7, 2017

(54) METHOD OF OPERATING AN ENGINE

(71) Applicant: Caterpillar Inc., Peoria, IL (US)

(72) Inventor: Amiyo K. Basu, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 263 days.

(21) Appl. No.: 14/559,978

(22) Filed: Dec. 4, 2014

(65) Prior Publication Data

US 2016/0160785 A1    Jun. 9, 2016

(51) Int. Cl.
```
F02D 41/00    (2006.01)
G01N 33/00    (2006.01)
F01N 3/20     (2006.01)
F01N 3/10     (2006.01)
F02D 41/14    (2006.01)
```

(52) U.S. Cl.
CPC ......... *G01N 33/0037* (2013.01); *F01N 3/208* (2013.01); *F02D 41/1462* (2013.01); *F01N 3/106* (2013.01); *F01N 3/2066* (2013.01); *F01N 2430/00* (2013.01); *F01N 2560/026* (2013.01); *F01N 2560/06* (2013.01); *F01N 2560/08* (2013.01); *F01N 2560/14* (2013.01); *F01N 2610/02* (2013.01); *F01N 2900/0412* (2013.01); *F01N 2900/0601* (2013.01); *F01N 2900/08* (2013.01); *F01N 2900/1402* (2013.01); *F02D 41/1446* (2013.01); *F02D 41/1448* (2013.01); *F02D 2200/0414* (2013.01); *F02D 2200/0418* (2013.01); *F02D 2200/1004* (2013.01); *F02D 2200/703* (2013.01); *F02D 2250/36* (2013.01)

(58) Field of Classification Search
CPC ..... F02D 2041/1433; F02D 2041/0072; F02D 41/1462; F02D 41/146; F02D 41/18; F02D 2200/0414; F02D 2200/0418; F02D 2200/0406; G01N 33/0037; F01N 3/208; F01N 3/106; F01N 2560/026; F01N 2560/06; F01N 2560/08; G01L 23/24
USPC ......... 701/104, 103, 109; 73/114.31, 114.33, 73/114.34, 114.37
See application file for complete search history.

(56) References Cited

U.S. PATENT DOCUMENTS

| | | | |
|---|---|---|---|
| 4,672,561 | A | 6/1987 | Katayama et al. |
| 5,735,245 | A | 4/1998 | Kubesh et al. |
| 6,508,242 | B2 | 1/2003 | Jaliwala et al. |
| 6,522,994 | B1 | 2/2003 | Lang |
| 6,575,148 | B1 | 6/2003 | Bhargava et al. |

(Continued)

*Primary Examiner* — Hai Huynh
*Assistant Examiner* — Gonzalo Laguarda
(74) *Attorney, Agent, or Firm* — James S. Bennin

(57) ABSTRACT

A method of operating an engine is provided. The method includes determining a temperature and a pressure of intake air, and a temperature and a pressure of exhaust generated by the engine. The method includes determining a work performed by the engine based at least on an engine speed of the engine, and determining heating losses of the engine. The method includes determining an enthalpy of the intake air based at least on the work, the heating losses, a heating value of a fuel used for combustion within the engine, and the temperature and the pressure of the exhaust. The method includes determining a humidity value of the intake air based on the enthalpy, temperature and pressure of the intake air and determining an amount of NOx based on the humidity value. The method further includes controlling an operation of the engine based on the determined amount of NOx.

20 Claims, 4 Drawing Sheets

(56) References Cited

U.S. PATENT DOCUMENTS

| | | |
|---|---|---|
| 6,662,795 B2 | 12/2003 | Baldwin et al. |
| 6,708,496 B2 | 3/2004 | Gadde et al. |
| 6,728,625 B2 | 4/2004 | Strubhar et al. |
| 6,868,368 B1 | 3/2005 | Lang |
| 7,246,604 B2 | 7/2007 | Cullen |
| 7,597,093 B2 | 10/2009 | Totten et al. |
| 7,958,866 B2 | 6/2011 | Thomas |
| 8,103,429 B2 | 1/2012 | Sivasubramaniam et al. |
| 8,813,690 B2 | 8/2014 | Kumar et al. |
| 2002/0185107 A1* | 12/2002 | Kubesh ................ F02D 41/146 123/406.44 |
| 2004/0144082 A1 | 7/2004 | Mianzo et al. |
| 2012/0260886 A1* | 10/2012 | Mulye ................... F02B 47/02 123/25 C |
| 2015/0275795 A1* | 10/2015 | Cygan, Jr. ........... F02D 41/0255 701/102 |
| 2015/0330326 A1* | 11/2015 | Shaver ............... F02D 41/0062 123/445 |
| 2016/0047337 A1* | 2/2016 | Leone ...................... F01L 1/34 123/406.12 |
| 2016/0131089 A1* | 5/2016 | Lahti ................ F02M 25/0753 60/605.2 |

\* cited by examiner

METHOD OF OPERATING AN ENGINE

TECHNICAL FIELD

The present disclosure relates to a method of operating an engine, and more specifically to a system and method for operating an engine by estimating an amount of NOx in an engine exhaust.

BACKGROUND

Internal combustion engines generate power by combusting a mixture of a fuel and air. In some cases, the combustion process may result in formation of nitrogen oxides (NOx) among other gases, particulates in an exhaust. The NOx is considered as a pollutant. Therefore, vehicles or machines fitted with the internal combustion engines have to comply with regulatory emission standards that limit an amount of NOx in the exhaust generated by the engine. As such, it is essential to monitor the amount of NOx in the engine and accordingly control operations of the engine based on the amount of NOx. Various methods are proposed for determining the amount of NOx. One such method includes using a NOx sensor for determining the amount of NOx. However such implementation is costly. Additionally, the operating conditions within the machine may sometimes render the sensors faulty.

For reference, U.S. patent publication No. 2004/0144082 relates to a controller for controlling nitrogen oxides (NOx) emissions from a combustion engine based on estimating a parameter for the engine. The controller is capable of adjusting cylinder temperature based on the estimated parameter for controlling NOx emissions.

SUMMARY OF THE DISCLOSURE

In one aspect of the present disclosure, a method of operating an engine is provided. The method includes determining a temperature and a pressure of the intake air, and a temperature and a pressure of exhaust generated by the engine. The method also includes determining a work performed by the engine based at least on an engine speed of the engine and determining heating losses of the engine. The method includes determining an enthalpy of the intake air based at least on the work performed by the engine, the heating losses of the engine, a heating value of a fuel used for combustion within the engine, and the temperature and the pressure of the exhaust. The method also includes determining a humidity value of the intake air based on the enthalpy, temperature and pressure of the intake air and determining an amount of NOx based at least on the humidity value of the intake air. The method further includes controlling an operation of the engine based on the determined amount of NOx.

In another aspect of the present disclosure, a control system for an engine is provided. The control system includes a first sensor configured to generate a signal indicative of a temperature of the intake air and a second sensor configured to generate a signal indicative of a pressure of the intake air. The control system also includes a third sensor configured to generate a signal indicative of a temperature of the exhaust and a fourth sensor configured to generate a signal indicative of a pressure of the exhaust. The control system further includes a controller communicably coupled with the first sensor, the second sensor, the third sensor and the fourth sensor. The controller is configured to determine a work performed by the engine based at least on an engine speed of the engine and determine heating losses of the engine. The controller is also configured to determine an enthalpy of the intake air based at least on the work performed by the engine, the heating losses of the engine, a heating value of a fuel used for combustion within the engine, and the temperature and the pressure of the exhaust. The controller is also configured to determine a humidity value of the intake air based on the enthalpy, temperature and pressure of the intake air and determining an amount of NOx based at least on the humidity value of the intake air. The controller is further configured to control operation of the engine based on the amount of NOx.

In yet another aspect of the present disclosure, a method of operating an engine having a NOx sensor is provided. The method includes determining a temperature and a pressure of the intake air, and a temperature and a pressure of exhaust generated by the engine. The method also includes determining a work performed by the engine based at least on an engine speed of the engine and determining heating losses of the engine. The method includes determining an enthalpy of the intake air based at least on the work performed by the engine, the heating losses of the engine, a heating value of a fuel used for combustion within the engine, and the temperature and the pressure of the exhaust. The method also includes determining a humidity value of the intake air based on the enthalpy, temperature and pressure of the intake air and determining a first amount of NOx based at least on the humidity value of the intake air. The method also includes comparing the first amount of NOx with a second amount of NOx detected by the NOx sensor and controlling the engine based on the first amount of NOx if a difference between the first amount of NOx and the second amount of NOx exceeds a predetermined threshold.

DETAILED DESCRIPTION

Figure 1:
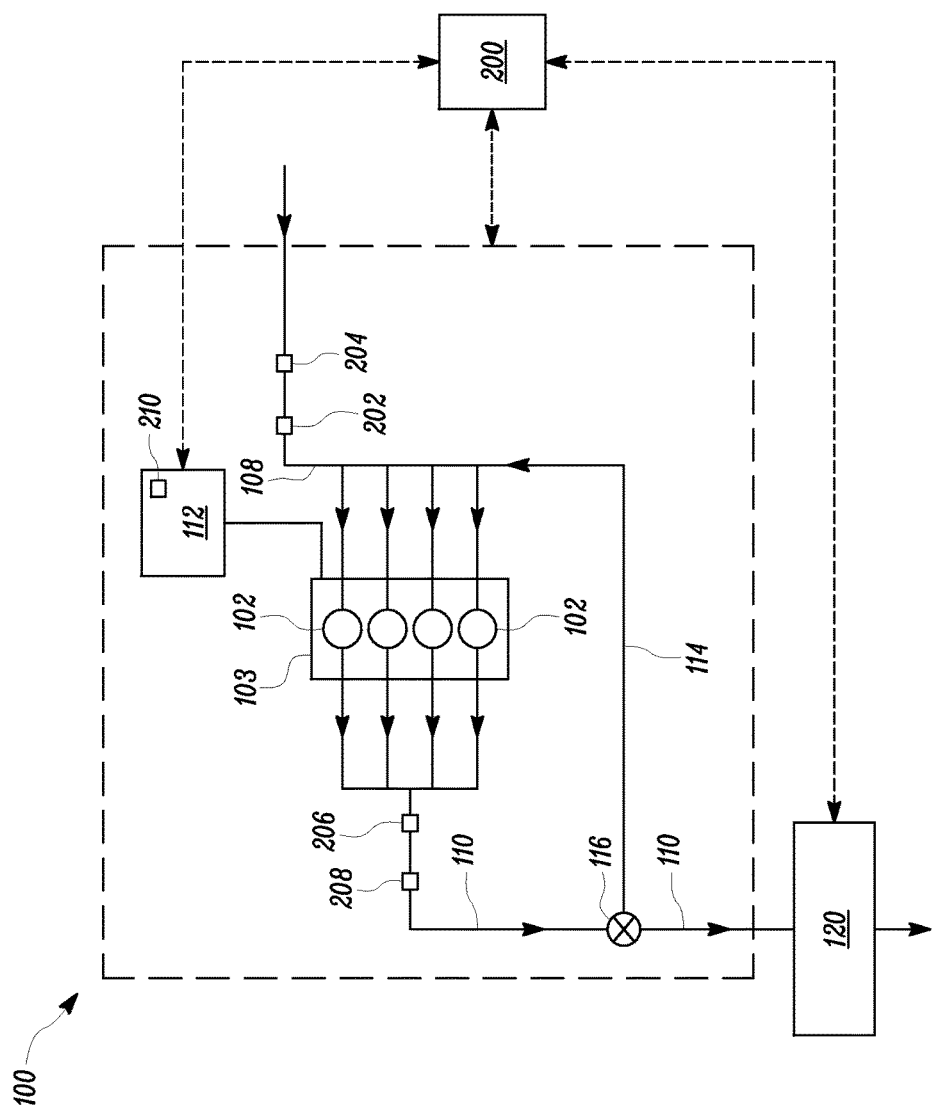
FIG. 1 is a schematic view of an exemplary engine.

Wherever possible, the same reference numbers will be used throughout the drawings to refer to the same or the like parts. FIG. 1 is a schematic representation of an exemplary engine 100. The engine 100 may be an internal combustion engine 100 which runs on fuels, such as diesel, gasoline, gaseous fuels, or a combination thereof. The engine 100 may power various types of machines associated with an industry including, but not limited to, transportation, construction, mining, agriculture, forestry, waste management and material handling.

While FIG. 1 depicts an inline-type engine 100, it will be appreciated that the embodiments described herein may be used in any suitable configuration of the engine 100, including, but not limited to, V-type, radial, rotary or the like. Further, the engine 100 may be of any type, such as diesel or gasoline compression ignition engine, spark ignition engine 100, direct or port injection engine, and the like.

The engine 100 includes an engine body 103 defining a plurality of cylinders 102. Although, four cylinders 102 are shown, it should be noted that the number of cylinders 102, and their arrangements in the engine 100 are not restricted to the above configuration.

The cylinders 102 may be configured to slidably receive pistons (not shown) therein. Further, the cylinders 102 may define an intake port (not shown) and an exhaust port (not shown) therein. The cylinders 102 receives intake air from an intake line 108 through the intake port. Various other components for example, an air filter (not shown) and a turbo charger (not shown) may be arranged in the intake line 108 through which the intake air may pass. The cylinders 102 may be supplied with the fuel for combustion from devices such as, fuel injectors, admission valves and the like depending on the type of the engine 100. A mass ratio of the intake air and the fuel supplied to the cylinders 102 for combustion may be defined as an air/fuel (AF) ratio.

In some examples, a time of injection of the fuel into the cylinder 102 may be defined as an ignition timing (IT). The time of injection may correspond to a position of the piston within the corresponding cylinder 102. In other examples, where the combustion of the fuel is through spark ignition, the ignition timing (IT) may correspond to a time of providing the spark.

Further, the engine 100 includes an exhaust line 110 configured to receive exhaust generated by the engine 100 during combustion through the exhaust port of the corresponding cylinder 102. The engine 100 also includes a coolant system 112 configured to supply a coolant, for example, water to the engine 100. The engine 100 may utilize the coolant to cool one or more components of the engine 100 such as, the exhaust line 110. The coolant may be provided by the coolant system 112 including a radiator, a cooling fan, a pump and coolant conduits for circulating the coolant through a body of the engine 100 and back to the radiator. The coolant system 112 may also include one or more valves for regulating a flow of the coolant.

In an embodiment, the engine 100 may include an Exhaust Gas Recirculation (EGR) line 114 and an associated EGR control valve 116. The EGR line 114 may be in fluid communication with the exhaust line 110 and the intake line 108 via the EGR control valve 116. The EGR line 114 may recirculate the exhaust received from the exhaust line 110 or the cylinders 102 to the intake line 108 upon opening the EGR control valve 116. The EGR control valve 116 may be fully opened, partially opened or fully closed. Accordingly, the EGR control valve 116 may be regulated to control an EGR flow rate (mEGR), thereby controlling an amount of the exhaust to be passed to the intake line 108. Additional components (not shown), such as one or more coolers, filters, and the like, may also be provided in the EGR line 114.

The exhaust leaving the engine 100 is conveyed through the exhaust line 110 and discharged into the surroundings via an exhaust outlet (not shown). The exhaust may include at least one of nitrogen (N2), water vapor (H20), carbon-dioxide (CO2), carbon-monoxide (CO), hydrocarbons (HC), nitrogen oxides (NOx), particulate matter, such as soot, among other material.

In an embodiment, an exhaust aftertreatment system 120 may be associated with the engine 100. The exhaust aftertreatment system 120 is configured to treat the exhaust from the engine 100. The exhaust aftertreatment system 120 may include a diesel oxidation catalyst (DOC) (not shown) arranged in the exhaust line 110. The DOC is configured to generate nitrogen dioxide ($NO_2$), which is required by a selective catalytic reduction (SCR) catalyst (not shown) that is arranged downstream of the DOC. The SCR catalyst is configured to convert oxides of nitrogen ($NO_X$) into diatomic nitrogen ($N_2$) and water ($H_2O$) using the $NO_2$ generated by the DOC.

The SCR conversion process may additionally requires a controlled or metered amount of a reducing agent. Accordingly, the exhaust aftertreatment system 120 may include one or more injection devices upstream of the SCR catalyst configured to inject a reducing agent into the exhaust in the exhaust line 110. The reducing agent may be urea ($CO(NH_2)_2$) or ammonia ($NH_3$). As such, the exhaust from the engine 100 may pass through the SCR catalyst before being discharged into the surroundings via the exhaust outlet.

Figure 2:
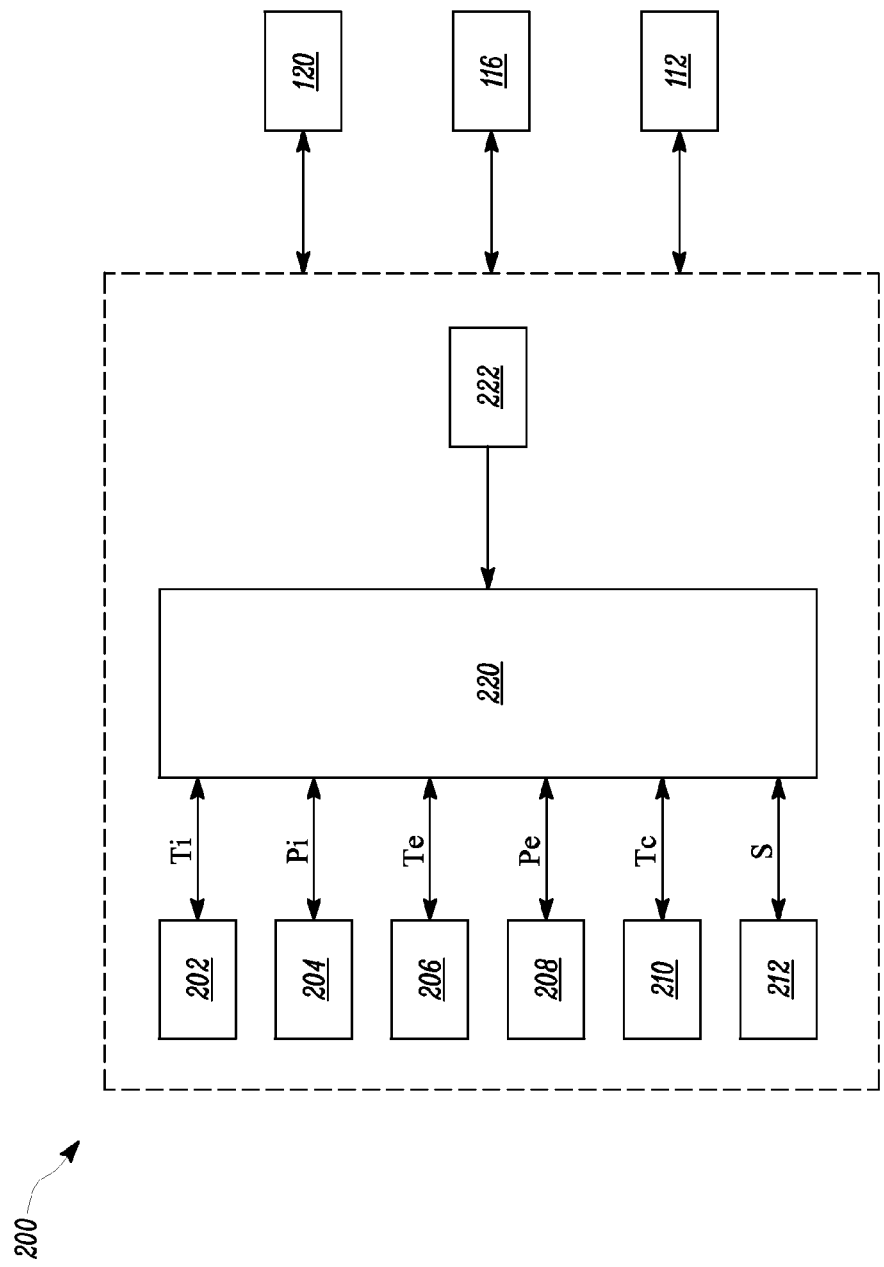
FIG. 2 is a block diagram of a control system for operating the engine, according to an embodiment of the present disclosure.
Figure 3:
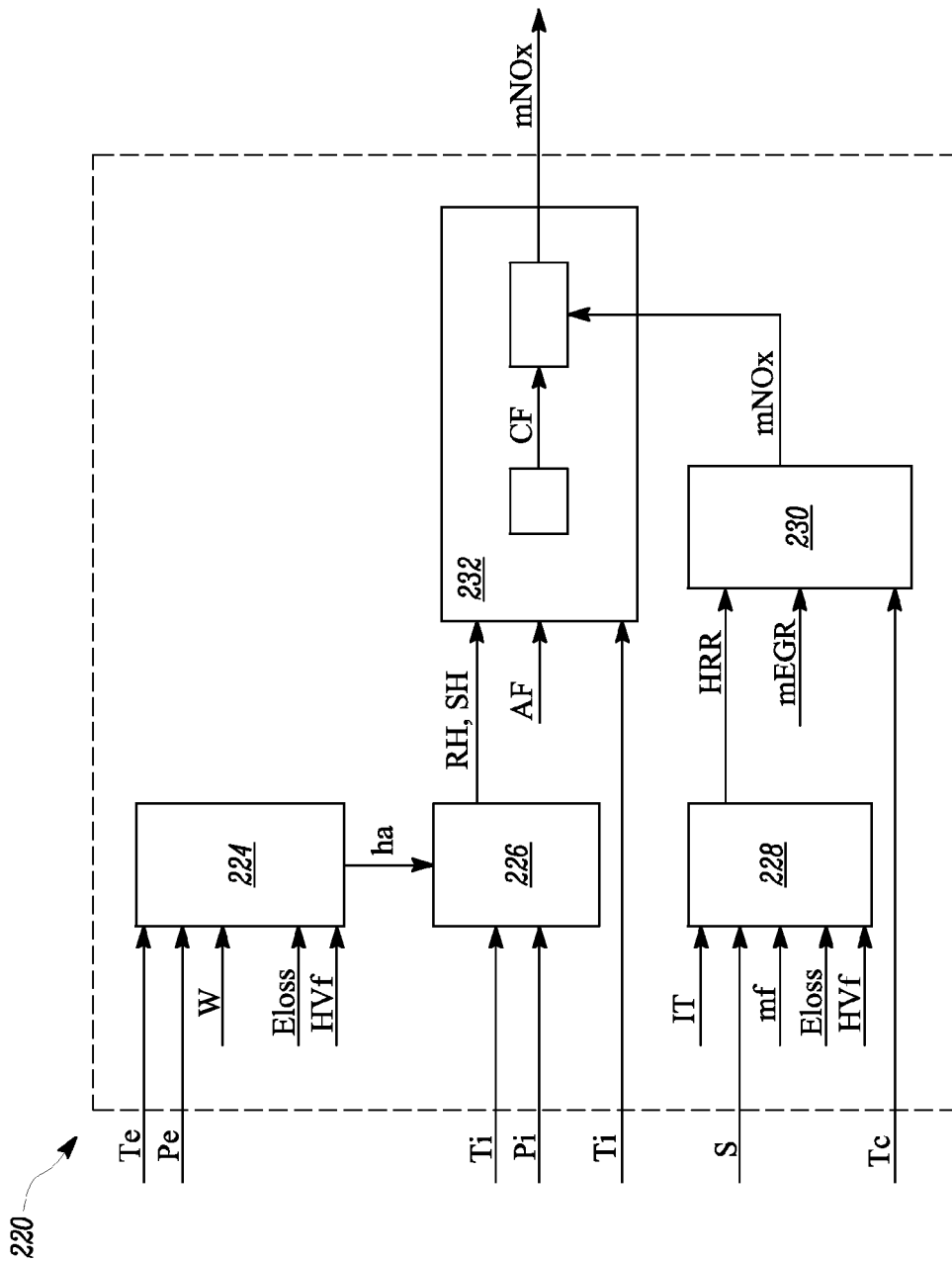
FIG. 3 is a control diagram for the control system of FIG. 2, according to an embodiment of the present disclosure.

The engine 100 may include a control system 200 configured to control an operation of the engine 100. Specifically, the control system 200 may be configured to determine an amount of NOx (mNOx) present in the exhaust and accordingly control an operation of the engine 100 and/or other components associated therewith. In an embodiment, the control system 200 is an electronic control unit (ECU) of the engine 100. Referring to FIG. 2, a block diagram of the control system 200 is illustrated, according to an embodiment of the present disclosure. Referring to FIG. 3, a control diagram for an operation of the engine 100 via the control system 200 is illustrated. The control system 200 will be explained hereinafter with reference to FIGS. 1 to 3.

The control system 200 includes a first sensor 202 and a second sensor 204. The first sensor 202 is configured to generate a signal (S1) indicative of a temperature (Ti) of the intake air. Specifically, the temperature (Ti) may be indicative of a dry-bulb temperature of the intake air. The first sensor 202 may be disposed in the intake line 108. The second sensor 204 is configured to generate a signal (S2) indicative of a pressure (Pi) of the intake air. In an embodiment, the signal (S2) may be indicative of an atmospheric pressure. Further, the second sensor 204 may be disposed in the intake line 108 of the engine 100.

The control system 200 may also include a third sensor 206 and a fourth sensor 208 disposed in the exhaust line 110. The third sensor 206 is configured to generate a signal (S3) indicative of a temperature (Te) of the exhaust. The fourth sensor 208 is configured to generate a signal (S4) indicative of a pressure (Pe) of the exhaust. In an embodiment, the control system 200 may also include a fifth sensor 210 configured to generate a signal (S5) indicative of a temperature (Tc) of the coolant utilized by the engine 100.

The control system 200 may further include an engine speed sensor 212 configured to deliver a signal (S6) indicative of an engine speed (S) of the engine 100. The engine speed sensor 212 may be associated with a crankshaft, a camshaft or any other component of the engine 100.

The control system 200 further includes a controller 220 configured to determine the amount of NOx (mNOx) in the exhaust and accordingly control an operation of the engine 100. The controller 220 may be configured to determine the amount of NOx (mNOx) based at least on a humidity value of the intake air which will be explained in detail hereinafter.

The controller 220 may embody a single microprocessor or multiple microprocessors configured for receiving signals from the components of the control system 200. Numerous commercially available microprocessors may be configured to perform the functions of the controller 220. It should be appreciated that the controller 220 may embody a machine microprocessor capable of controlling numerous machine functions. A person of ordinary skill in the art will appreciate that the controller 220 may additionally include other components and may also perform other functions not described herein. The controller 220 can also be configured to receive inputs from an operator via a user interface (not shown).

The controller 220 is electrically connected to various elements of the control system 200 10, as well as various input devices for determining the amount of NOx (mNOx) and commanding the operation of the engine 100. As illustrated in FIG. 2, the controller 220 may be communicably coupled to the sensors 202, 204, 206, 208, 210, 212 to receive respective signals related to the operating conditions of the engine 100. The controller 220 may also be electrically connected to various input devices to receive one or more parameters related to the engine operation. For example, the input device may be a pedal, a lever, a joystick, or any appropriate input device for controlling an operation of the engine 100.

Further, a memory 222 associated with the controller 220 may include data regarding one or more properties of the fuels available for use by the engine 100, the intake air, the exhaust and the like. Examples of the property data corresponding to a fuel available to the engine 100 may include a density or specific gravity of the fuel, the heat of combustion of the fuel expressed as, for example, the heating value (HVf) indicating the energy released by the fuel during combustion, and the like. The heating value (HVf) of the fuel is a characteristic of each fuel and may be measured in units of energy per unit of the fuel.

The data may also include properties of the intake air such as, a molecular weight, densities and the like. Further, the memory 222 may include various psychrometric data, reference maps, look-up tables, and the like related to the intake air.

Further, the memory 222 may include any data necessary for the controller 220 to determine the work (W) performed by the engine 100, the heating losses (Eloss) of the engine 100 as discussed further below. In one example, the memory 222 may be internal to the control system 200 and/or the controller 220. In another example, the memory 222 may be a database external to the control system 200 and/or the controller 220, and the data from the memory 222 may be communicated to the controller 220.

As illustrated in FIG. 3, the controller 220 may include multiple control modules for implementing various control strategies associated with the engine 100.

The controller 220 includes a first module 224 configured to determine the enthalpy (ha) of the intake air (S1)(S2). The first module 224 determines the enthalpy (ha) of the intake air as a function of the heating value (HVf) of the fuel, the work (W) performed by the engine 100, the heating losses (Eloss), the temperature (Te) and the pressure (Pe) of the exhaust.

(S3)(S4) During combustion, energy of the air-fuel mixture is converted to work that is performed by the engine 100, energy of exhaust gases, and energy or heating losses. According to an exemplary aspect of the present disclosure, an energy model for determining the enthalpy (ha) of the intake air is described below. The energy model may include determining the enthalpy (ha) of the intake air as a function of various energies associated with the combustion.

The energy model employs conservation equations pertaining to a control volume CV to determine the enthalpy (ha) of the intake air. In this case, a combustion chamber defined between the piston and a cylinder head (not shown) of the engine body 103 may be treated as the control volume CV. The conservation equations may be related to a mass conservation and energy conservation for the control volume CV. According to mass conservation, a mass entering the control volume is equal to a mass leaving the control volume. Further, the energy conservation for the control volume CV is indicated by equation (A):

(rate of energy flow of the intake air into CV)=(rate of work done)+(rate of heat losses out of CV)+ (rate of energy flow out of CV)−(rate of energy flow of the fuel into CV)    (A)

Where the rate of energy flow into CV of the intake air may be dependent on the enthalpy (ha) of the intake air. The rate of energy flow of the fuel into the CV may be based on by the heating value (HVf). Further, the rate of energy flow out of CV may be determined based on the temperature (Te) and the pressure (Pe) of the exhaust.

Therefore, based on the conservation equations, the enthalpy (ha) of the intake air may be determined as a function of the heating value (HVf) of the fuel, the work (W) performed by the engine 100, the heating losses (Eloss), and the temperature (Te) and the pressure (Pe) of the exhaust. This is indicated by the equation (B):

Enthalpy (ha) of the intake air=F((HVf),W,(Eloss), Te,Pe)    (B)

The first module 224 may obtain the heating value (HVf) of the fuel stored in the memory 222. Further, the first module 224 may determine the work (W) performed by the engine 100 based at least on the engine speed (S). In the illustrated embodiment of FIG. 3, the first module 224 may receive the signal (S6) indicative of the engine speed (S) from the engine speed sensor 212. However, in other embodiments, the first module 224 may be communicably coupled to input devices such as, the pedal, the joystick, the lever to determine the engine speed (S). Alternatively, the first module 224 may determine the engine speed (S) based on parameters such as, an amount of the fuel supplied for combustion. Further, the first module 224 may determine the work (W) performed by the engine 100 from a reference map, lookup table or may be calculated based on the engine speed (S) and other related parameters, for example, torque of the engine 100.

Alternatively, the first module 224 may determine the work (W) performed based on a load indicative signal provide by a load sensor (not shown). The load sensor may be operatively coupled to various components of the engine 100 such as, but not limited to, a camshaft, a crankshaft or other appropriate component to sense the work (W) performed by the engine 100.

The first module 224 may determine the heating losses (Eloss) associated with the combustion in the engine 100. The heating losses (Eloss) may be various energy losses and/or heating losses due to conduction, radiation and convective heat transfer from walls of the cylinder 102, the cylinder head, the piston and the like to the surroundings. The heating losses (Eloss) may also include various frictional losses. Accordingly, the first module 224 may determine the heating losses (Eloss) based on related parameters, for example, thermal conduction of walls of the cylinder 102, size of the engine 100, the temperature (Te) of the exhaust and the like.

The first module 224 may receive the signals (S3) and (S4) indicative of the temperature (Te) and the pressure (Pe) of the exhaust from the third and fourth sensors 206, 208, respectively.

Further, the energy model may include a mathematical equation relating the enthalpy (ha) of the intake air to the above discussed parameters (HVf), (W), (Eloss), (Te) and (Pe). The mathematical equation may be determined based on a multiple polynomial regression model, a physics based model, a neural network model or any other model or algorithm known in the art.

In various other embodiments, the energy model may include reference maps, look-up tables stored in the memory 222 for determining the enthalpy (ha) of the intake air as a function of the parameters (HVf), (W), (Eloss), (Te) and (Pe). Accordingly, the second module 226 may implement the energy model to determine the enthalpy (ha) of the intake air.

The controller 220 includes a second module 226 configured to determine the humidity value of the intake air based on the enthalpy (ha), the temperature (Ti) and the pressure (Pi) of the intake air. Specifically, the second module 226 may determine a relative humidity (RH) of the intake air based on the enthalpy (ha), the temperature (Ti) and the pressure (Pi) of the intake air. This is indicated by the equation (C):

$$\text{Relative Humidity (RH)}=F((ha),(Ti),(Pi)) \qquad (C)$$

The second module 226 may be configured to receive the signals (S1) and (S2) indicative of the temperature (Ti) and the pressure (Pi) of the intake air from the first and second sensors 202, 204 respectively. Further, the second module 226 receives the enthalpy (ha) of the intake air from the first module 224. Based on the enthalpy (ha), the temperature (Ti) and the pressure (Pi) of the intake air, the second module 226 may determine other parameters associated with the intake air such as, but not limited to, the relative humidity (RH) of the intake air.

In one embodiment, the second module 226 may refer to a psychrometric chart to determine the relative humidity (RH) of the intake air. The psychrometric chart may include physical and thermal properties of gas-vapor mixtures represented in a graphical form. For example, the psychrometric chart allows the parameters such as, the relative humidity (RH) of air-water vapor mixture to be determined from independent parameters such as, temperature, pressure, enthalpy etc.

In another embodiment, the second module 226 may refer to one or more reference maps, lookup tables stored in the memory 222 to determine the relative humidity (RH) of the intake air. In yet another embodiment, the second module 226 may calculate the relative humidity (RH) of the intake air from a predetermined mathematical equation. The mathematical equation may include a multiple polynomial regression model, a physics based model, a neural network model or any other model or algorithm known in the art.

Additionally, the second module 226 may determine a specific humidity (SH) of the intake air based on the relative humidity (RH) and the pressure (Pi) of the intake air.

The control system 200 may further include a third module 228 configured to determine a Heat Release Rate (HRR) and/or heat release from the combustion. In this example, the HRR is indicative of a rate of heat generated due to the combustion of the air-fuel mixture. According to an exemplary aspect of the present disclosure, the HRR may be determined as a function of engine parameters such as, the ignition timing (IT), a fuel mass flow rate (mf) supplied to the cylinders 102, the engine speed (S), the heating value (HVf) of the fuel, the heating losses (Eloss). This is indicated by the equation (D):

$$\text{Heat Release Rate(HRR)}=F((IT),(HVf),(S),(Eloss), (mf)) \qquad (D)$$

The third module 228 may obtain the heating losses (Eloss) determined by the first module 224. The third module 228 may obtain the heating value (HVf) of the fuel stored in the memory 222.

The controller 220 may further include a fourth module 230 configured to determine the amount of NOx (mNOx) According to one aspect of the present disclosure, the fourth module 230 may implement an exemplary NOx model to determine the amount of NOx (mNOx). According to the NOx model, the amount of NOx (mNOx) may be determined as a function of the HRR.

Further, excess oxygen in the intake air may react with nitrogen in the combustion products to form the NOx. The NOx model relates the excess oxygen in the intake air to the HRR. As such, the amount of NOx (mNOx) may be determined as a function of the HRR. Additionally, the NOx model may also factor in the temperature (Tc) of the coolant to determine the amount of NOx (mNOx). In an embodiment, for engines configured with the EGR line 114 and the EGR control valve 116, the NOx model may also factor in the dependence of the amount of NOx (mNOx) on the EGR flow rate (mEGR). As such, the amount of NOx (mNOx) may be determined as a function of the HRR, and optionally the temperature (Tc) of coolant and the EGR flow rate (mEGR). This is indicated by the equation (E):

$$\text{Amount of NOx(mNOx)}=F(HRR,(mEGR),(Tc)) \qquad (E)$$

In an example, the NOx model may include a mathematical equation relating the amount of NOx (mNOx) to the above discussed parameters HRR, (mEGR) and (Tc). The mathematical equation may be determined based on a multiple polynomial regression model, a physics based model, a neural network model or any other model or algorithm known in the art.

In other examples, the NOx model may include reference maps or look-up tables stored in the memory 222 to determine the amount of NOx (mNOx) as a function of the HRR, (mEGR) and (Tc). Accordingly, the fourth module 230 may implement the NOx model to determine the amount of NOx (mNOx) in the exhaust.

The controller 220 further includes a fifth module 232 configured to modify the amount of NOx (mNOx) based on a humidity value of the intake air. In an example, the humidity value may be the specific humidity (SH) of the intake air determined based on the relative humidity (RH) of the intake air. Further, the fifth module 232 may determine a correction factor (CF) for the amount of NOx (mNOx) based on the specific humidity (SH) of the intake air. The fifth module 232 may receive the specific humidity (SH) of the intake air from the second module 226. Further, the fifth module 232 may also receive the signal (S1) indicative of the temperature (Ti) of the intake air from the first sensor 202. The fifth module 232 may determine the correction factor (CF) as a function of the specific humidity (SH) of the intake air. In an example, for a heavy duty engine, the correction factor (CF) may be dependent on the specific humidity (SH) of the intake air. In another example, the correction factor (CF) may be determined further as a function of one or more engine parameters such as, the temperature (Ti) of the intake air, AF ratio and the like. This may be indicated by the equation (E):

$$\text{correction factor(CF)}=F((SH),(Ti),(AF)) \qquad (F)$$

The fifth module 232 may modify the amount of NOx (mNOx) based on the correction factor (CF). In an example, the fifth module 232 may modify the amount of NOx (mNOx) by multiplying the correction factor (CF) with the determined amount of NOx (mNOx).

In an another embodiment, the controller 220 may be configured to determine the amount of NOx (mNOx) directly as a function of the humidity value among other relevant parameters such as, the AF ratio, the temperature (Ti) and the pressure (Pe) of the intake air and the engine speed (S).

The controller 220 may be configured to control an operation of the engine 100 based on the amount of NOx (mNOx). The controller 220 may be electrically connected to various components of the engine 100 in order to regulate one or more parameters associated with the engine 100.

In an example, the controller 220 may regulate the EGR flow rate (mEGR) based on the amount of NOx (mNOx). Consequently, the EGR control valve 116 may be connected to the controller 220 to receive signals corresponding to controlling flow of the exhaust. In another example, the controller 220 may regulate the ignition timing (IT) based on the amount of NOx (mNOx). Consequently, the controller 220 may generate signals to control the fuel injectors 38 or the spark plugs. In yet another example, the controller 220 may also regulate the temperature (Tc) of the coolant based on the amount of NOx (mNOx). Consequently, the coolant system 112 may be communicably coupled to the controller 220 to receive signals corresponding to controlling the temperature (Tc) of the coolant. In various other examples, the controller 220 may control other engine parameters such as, but not limited to, a flow rate of the fuel, a flow rate of the intake air, a fuel injection pressure, and the like based on the amount of NOx (mNOx).

Further, the controller 220 may optionally or additionally regulate operations of various other components associated with the engine 100 such as, but not limited to, the exhaust aftertreatment system 120. In one embodiment, the controller 220 may regulate an amount of the reducing agent dispensed from the exhaust aftertreatment system 120 into the exhaust line 110.

In an alternative embodiment, the controller 220 may compare the amount of NOx (mNOx) with a predetermined NOx threshold. The controller 220 may adapt one or more control strategies as discussed above to reduce the amount of NOx (mNOx) below the predetermined NOx threshold if the amount of NOx (mNOx) is greater than the predetermined NOx threshold.

Although, control of specific parameters or systems are described above, the controller 220 may control other operations of the engine 100 based on the amount of NOx (mNOx). Moreover, the controller 220 may also determine additional parameters associated with the exhaust based on the above discussed models.

Additionally or optionally, the controller 220 may trigger an alert for the operator when the amount of NOx (mNOx) exceeds the predetermined NOx threshold. The alert may be audible, visible, tactile, or a combination thereof.

In one embodiment, the engine 100 may be configured with a NOx sensor disposed in the exhaust line 110. Further, the NOx sensor may be disposed upstream of the exhaust aftertreatment system 120. In such a case, the controller 220 may determine the amount of NOx (a first amount of NOx) based on the NOx model described above and the NOx sensor may also detect an amount of NOx (a second amount of NOx) in the exhaust. The controller 220 compares the first amount of NOx to the second amount of NOx to determine if a difference between the first amount of NOx and the second amount of NOx exceeds a predetermined threshold. Further, the controller 220 may operate the engine 100 as discussed above based on the first amount of NOx if the difference exceeds the predetermined threshold.

Additionally, based on the comparison between the first amount of NOx that is determined theoretically and the second amount of NOx that is detected by the NOx sensor, the controller 220 may determine a health of the NOx sensor. Further, the controller 220 may determine the NOx sensor as faulty if the difference between the first amount of NOx and the second amount of NOx exceeds the predetermined threshold. In such a case, the controller 220 may additionally generate a flag to the NOx sensor indicating that the NOx sensor is faulty. Optionally, the controller 220 may also generate an alarm which may be audible, optical sound, or a light to the operator.

INDUSTRIAL APPLICABILITY

The control system 200 of the present disclosure is configured to control operations of the engine 100 based on the amount of NOx (mNOx). Further, the controller 220 may be configured to determine the amount of NOx (mNOx) based on the humidity value of the intake air. Further, the controller 220 may also factor in various other parameters such as, the EGR flow rate (mEGR), the coolant temperature (Tc) of the intake air and the like to determine the amount of NOx (mNOx) in the exhaust.

Figure 4:
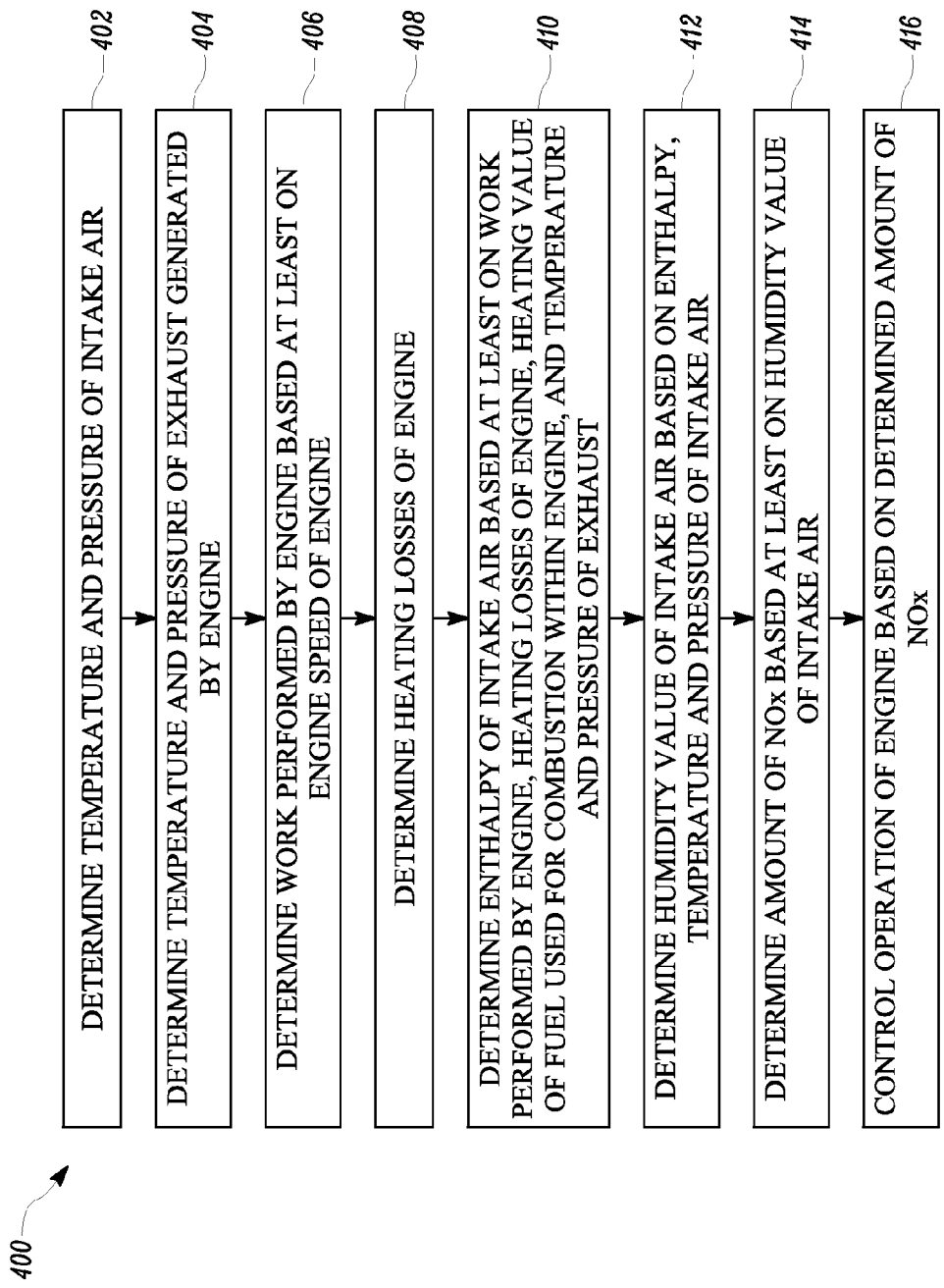
FIG. 4 is a flowchart for a method of operating an engine, according to an embodiment of the present disclosure.

Referring to FIG. 4, a flowchart for a method 400 of operating the engine 100 is illustrated. In an embodiment, one or more steps of the method 400 may be implemented via the control system 200. At step 402, the method 400 includes determining the temperature (Ti) and the pressure (Pi) of the intake air. At step 404, the method 400 includes determining the temperature (Te) and the pressure (Pe) of the exhaust.

At step 406, the method 400 includes determining the work (W) performed by the engine 100 based at least on the engine speed (S). At step 408, the method 400 includes determining the energy losses of the engine 100.

At step 410, the method 400 includes determining the enthalpy (ha) of the intake air based at least on the enthalpy (ha) of the intake air, the work (W) performed by the engine 100, the heating losses (Eloss) of the engine 100, the heating value (HVf) of the fuel, and the temperature (Te) and the pressure (Pe) of the exhaust.

At step 412, the method 400 includes determining the humidity value of the intake air based on the enthalpy (ha) of the intake air, the temperature (Ti) and the pressure (Pi) of the intake air. The humidity value may be the relative humidity (RH) of the intake air. In an example, the relative humidity (RH) may be determined from the psychrometric chart corresponding to the determined enthalpy (ha), the temperature (Ti) and the pressure (Pi) of the intake air. Further, the specific humidity (SH) of the intake air may be determined based on the relative humidity (RH).

At step 414, the method 400 includes determining the amount of NOx (mNOx) based on the humidity value of the intake air. In an embodiment, the amount of NOx (mNOx) may be determined according to the NOx model as discussed above. Further, the correction factor (CF) may be determined based at least on the humidity value. Specifically, the correction factor (CF) may be determined based on the specific humidity (SH) of the intake air. In an embodiment, the correction factor (CF) may be determined further based on the temperature (Ti) of the intake air and the AF ratio. The method 400 further includes determining the amount of NOx (mNOx) further based on the correction factor (CF).

At step 414, the method 400 further includes determining the amount of NOx (mNOx) further based on the ignition timing (IT), the EGR flow rate (mEGR), the temperature (Tc) of the coolant.

At step 416, the method 400 includes controlling an operation of the engine 100 based on the amount of NOx (mNOx). In an embodiment, the method 400 may include controlling one or more parameters of the engine 100 such as, the EGR flow rate (mEGR), the temperature (Tc) of the coolant, the ignition timing (IT) and the like. In another embodiment, the method 400 may include controlling the exhaust aftertreatment system 120 based on the amount of NOx (mNOx).

The sequence of the steps 402, 404, 406, 408, 410, 412, 414 and 416, as described above is exemplary in nature, and the steps 402, 404, 406, 408, 410, 412, 414 and 416 may be implemented either simultaneously or in any other alternative sequence.

With implementation of the method 400, the amount of NOx (mNOx) may be determined based on theoretical calculations using various thermodynamic relations. Further, an operation of the engine 100 may be controlled based on the amount of NOx (mNOx) to reduce the amount of NOx (mNOx) so as to meet emission standards.

The control system 200 and the method 400 of the present disclosure may enable determination of the amount of NOx (mNOx) without requiring an additional NOx sensor. Further, the control system 200 and the method 400 may also enable determination of the humidity value of the intake air without requiring a humidity sensor. The parameters used for determining the amount of NOx (mNOx) may be already determined for implementing existing engine control strategies. Further, the control system 200 and the method 400 may also be used to detect a faulty NOx sensor and provide an alternative to determine the amount of NOx in case of NOx sensor failure.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A method of operating an engine, the method comprising:
   determining, by a controller, a temperature and a pressure of intake air;
   determining, by the controller, a temperature and a pressure of exhaust generated by the engine;
   determining, by the controller, a work performed by the engine based at least on an engine speed of the engine;
   determining, by the controller, heating losses of the engine;
   determining, by the controller, an enthalpy of the intake air based at least on the work performed by the engine, the heating losses of the engine, a heating value of a fuel used for combustion within the engine, and the temperature and the pressure of the exhaust;
   determining, by the controller, a humidity value of the intake air based on the enthalpy and the temperature and the pressure of the intake air;
   determining, by the controller, an amount of nitrogen oxides (NOx) as a function of the humidity value of the intake air; and
   controlling, by the controller, an operation of the engine based on the amount of NOx,
   controlling the operation of the engine based on the amount of NOx including controlling, based on the amount of NOx, one or more of:
      an Exhaust Gas Recirculation (EGR) flow rate for the engine,
      a temperature of a coolant utilized by the engine,
      an ignition timing of the engine,
      a flow rate of the fuel,
      a flow rate of the intake air, or
      a fuel injection pressure.

2. The method of claim 1, wherein the humidity value is determined using a psychrometric chart.

3. The method of claim 1 further comprising determining the amount of NOx further based on a mass ratio of the intake air and the fuel used for combustion within the engine.

4. The method of claim 1 further comprising determining the amount of NOx further based on the ignition timing of the engine.

5. The method of claim 1 further comprising determining the amount of NOx further based on the EGR flow rate for the engine.

6. The method of claim 1 further comprising determining the amount of NOx further based on the temperature of the coolant utilized by the engine.

7. The method of claim 1 further comprising controlling an exhaust aftertreatment system of the engine based on the amount of NOx.

8. A control system for an engine, the control system comprising:
   a first sensor configured to generate a signal indicative of a temperature of intake air;
   a second sensor configured to generate a signal indicative of a pressure of the intake air;
   a third sensor configured to generate a signal indicative of a temperature of exhaust;
   a fourth sensor configured to generate a signal indicative of a pressure of the exhaust; and
   a controller communicably coupled with the first sensor, the second sensor, the third sensor and the fourth sensor, the controller configured to:
      determine a work performed by the engine based at least on an engine speed of the engine;
      determine heating losses of the engine;
      determine an enthalpy of the intake air based at least on the work performed by the engine, the heating losses of the engine, a heating value of a fuel used for combustion within the engine, the temperature of the exhaust, and the pressure of the exhaust;
      determine a humidity value of the intake air based on the enthalpy, the temperature of the intake air, and the pressure of the intake air;
      determine an amount of nitrogen oxides (NOx) as a function of the humidity value of the intake air; and
      control, based on the amount of NOx, one or more of:
         a flow rate of the fuel,
         a flow rate of the intake air, or
         a fuel injection pressure.

9. The control system of claim 8, wherein the humidity value is determined using a psychrometric chart.

10. The control system of claim 8, wherein the amount of NOx is determined further based on a mass ratio of the intake air and the fuel used for combustion within the engine.

11. The control system of claim 8, wherein, based on the amount of NOx is, the controller is to control an ignition timing of the engine.

12. The control system of claim 8, wherein, based on the amount of NOx, the controller is to control an Exhaust Gas Recirculation (EGR) flow rate for the engine.

13. The control system of claim 8, wherein, based on the amount of NOx, the controller is to control a temperature of a coolant utilized by the engine.

14. The control system of claim 8, wherein the controller is further configured to control an exhaust aftertreatment system of the engine based on the amount of NOx.

15. A method of operating an engine having a NOx sensor, the method comprising:
    determining, by controller, a temperature and a pressure of intake air;
    determining, by the controller, a temperature and a pressure of exhaust generated by the engine;
    determining, by the controller, a work performed by the engine based at least on an engine speed of the engine;
    determining, by the controller, heating losses of the engine;
    determining, by the controller, an enthalpy of the intake air based at least on the work performed by the engine, heating losses of the engine and a heating value of a fuel used for combustion within the engine, and the temperature and the pressure of the exhaust;
    determining, by the controller, a humidity value of the intake air based on the enthalpy, the temperature and the pressure of the intake air;
    determining, by the controller, a first amount of NOx as a function of the humidity value of the intake air;
    comparing, by the controller, the first amount of NOx to a second amount of NOx detected by the NOx sensor; and
    controlling, by the controller, the engine based on the first amount of NOx if a difference between the first amount of NOx and the second amount of NOx exceeds a threshold,
        controlling the engine including controlling one or more of:
            an Exhaust Gas Recirculation (EGR) flow rate for the engine,
            a temperature of a coolant utilized by the engine,
            an ignition timing of the engine,
            a flow rate of the fuel,
            a flow rate of the intake air, or
            a fuel injection pressure.

16. The method of claim 15 further comprising determining the first amount of NOx further based on a mass ratio of the intake air and the fuel used for combustion within the engine.

17. The method of claim 15 further comprising determining the first amount of NOx further based on the ignition timing of the engine.

18. The method of claim 15 further comprising determining the first amount of NOx further based on the EGR flow rate for the engine.

19. The method of claim 15 further comprising determining the first amount of NOx further based on the temperature of the coolant utilized by the engine.

20. The method of claim 15 further comprising deactivating the NOx sensor if the difference between the first amount of NOx and the second amount of NOx exceeds the threshold.

* * * * *